United States Patent
Mizuno et al.

(10) Patent No.: US 9,962,647 B2
(45) Date of Patent: May 8, 2018

(54) ZERO GAS REFINER $CO_2$ CONCENTRATION MEASUREMENT DEVICE AND $CO_2$ CONCENTRATION MEASUREMENT SYSTEM

(71) Applicant: HORIBA, Ltd., Kyoto (JP)

(72) Inventors: Yusuke Mizuno, Kyoto (JP); Shigeyuki Akiyama, Kyoto (JP); Tomomichi Oka, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 392 days.

(21) Appl. No.: 14/735,965

(22) Filed: Jun. 10, 2015

(65) Prior Publication Data
US 2015/0360171 A1 Dec. 17, 2015

(30) Foreign Application Priority Data
Jun. 11, 2014 (JP) .................................. 2014-120442

(51) Int. Cl.
*B01D 53/26* (2006.01)
*G01N 33/00* (2006.01)
(Continued)

(52) U.S. Cl.
CPC ........... *B01D 53/261* (2013.01); *B01D 53/04* (2013.01); *G01N 21/3504* (2013.01);
(Continued)

(58) Field of Classification Search
CPC ...... B01D 53/04; B01D 53/261; B01D 53/00; G01N 33/0006; G01N 21/3504; G01N 33/004
(Continued)

(56) References Cited

U.S. PATENT DOCUMENTS 5,332,901 A * 7/1994 Eckles ............... G01N 21/3504
250/339.01
6,093,379 A * 7/2000 Golden .................. B01D 53/04
423/230
(Continued)

FOREIGN PATENT DOCUMENTS

JP 2000-180364 A 6/2000

*Primary Examiner* — Hezron E Williams
*Assistant Examiner* — Tarun Sinha
(74) *Attorney, Agent, or Firm* — Brooks Kushman P.C.

(57) ABSTRACT

This invention provides a zero gas refiner for $CO_2$ concentration measurement device that can continuously refine a zero gas that is preferable for $CO_2$ concentration measurement. This invention adopts the zero gas refiner comprising a water adsorbent and a $CO_2$ adsorbent that desorb an adsorbed component and restore an adsorption ability by being heated to a predetermined restoration temperature, a refiner body that adsorbs water and $CO_2$ in an introduced sample gas or air in this order by the use of the water adsorbent and the $CO_2$ adsorbent housed inside of the refiner body so as to refine a zero gas and that leads out the zero gas, and a heating mechanism that applies heat to the refiner body at a time when the adsorption ability of the water adsorbent or the $CO_2$ adsorbent drops to an amount that is less than or equal to a predetermined amount.

8 Claims, 8 Drawing Sheets

(51) Int. Cl.
*G01N 21/3504* (2014.01)
*B01D 53/04* (2006.01)
(52) U.S. Cl.
CPC ..... *G01N 33/004* (2013.01); *B01D 2253/104* (2013.01); *B01D 2253/106* (2013.01); *B01D 2253/108* (2013.01); *B01D 2253/116* (2013.01); *B01D 2257/504* (2013.01); *B01D 2257/80* (2013.01); *B01D 2259/402* (2013.01); *B01D 2259/40088* (2013.01); *Y02A 50/244* (2018.01); *Y02C 10/08* (2013.01)
(58) Field of Classification Search
USPC ....... 73/31.07, 1.07, 1.06; 96/122, 143, 146; 702/104
See application file for complete search history.

(56) References Cited

U.S. PATENT DOCUMENTS

| | | | |
|---|---|---|---|
| 2003/0178589 A1* | 9/2003 | Mori | A61B 5/0836 250/573 |
| 2012/0140216 A1* | 6/2012 | Miyaji | G01N 21/65 356/301 |
| 2014/0053729 A1* | 2/2014 | Crooks | B01D 53/0462 95/139 |
| 2015/0177103 A1* | 6/2015 | Brown | G01M 15/102 73/1.07 |

* cited by examiner

ZERO GAS REFINER CO₂ CONCENTRATION MEASUREMENT DEVICE AND CO₂ CONCENTRATION MEASUREMENT SYSTEM

CROSS-REFERENCE TO RELATED APPLICATION

This application claims priority to JP Application No. 2014-120442, filed Jun. 11, 2014, the disclosure of which is incorporated in its entirety by reference herein.

FIELD OF THE ART

This invention relates to a zero gas refiner for $CO_2$ concentration measurement device that measures a concentration of $CO_2$ contained in a measurement object gas such as air.

BACKGROUND ART

In case that a conventional $CO_2$ concentration measurement device measures a concentration of $CO_2$ of a sample gas whose $CO_2$ concentration is relatively low such as air or the like, a high accuracy is required. Then there is a case that the measurement accuracy is secured by conducting a drift correction or a zero correction on the $CO_2$ concentration measurement device. This correction is conducted by measuring a zero gas whose concentration of $CO_2$ as being a measuring object or a concentration of other measurement interference component (for example, water in case of measuring the $CO_2$ concentration by the infrared spectroscopy) is substantially zero.

There are two cases; one is to supply the zero gas by the use of a gas cylinder and the other is, as shown in Japanese Unexamined Patent Application Publication No. 2000-180364, to use a zero gas refiner to remove $CO_2$ or other measurement interference component from the air or the sample gas by the use of an adsorbent so as to refine the zero gas whose $CO_2$ concentration is substantially zero.

DISCLOSURE OF THE INVENTION

Problems to be Solved by the Invention

However, since the adsorbent used for the zero gas refiner described in the patent document 1 is soda lime that adsorbs $CO_2$ or other component by chemical bond and the soda lime is difficult to restore, it is necessary to exchange the adsorbent periodically. This makes the maintenance relatively complicated, although it is not so much complicated as exchanging the cylinder.

Then this present claimed invention intends to provide a zero gas refiner for $CO_2$ concentration measurement device that can continuously refine the zero gas whose quality is high and that is preferable for measuring a concentration of $CO_2$ such as air and that can be maintenance-free for a long period of time and a $CO_2$ concentration measurement system using the zero gas refiner for $CO_2$ concentration measurement device.

Means to Solve the Problems

More specifically, the zero gas refiner for $CO_2$ concentration measurement device (hereinafter also called just as a zero gas refiner) in accordance with this invention refines a zero gas containing no $CO_2$ as being a reference for a measurement of a $CO_2$ concentration and supplies the zero gas to a $CO_2$ concentration measurement device that measures a concentration of $CO_2$ in a sample gas.

The zero gas refiner for $CO_2$ concentration measurement device comprises a water adsorbent and a $CO_2$ adsorbent that desorb an adsorbed component and restore an adsorption ability by being heated to a predetermined restoration temperature, a refiner body that adsorbs water and $CO_2$ in an introduced sample gas or the air in this order by the use of the water adsorbent and the $CO_2$ adsorbent housed inside of the refiner body so as to refine the zero gas and that leads out the zero gas, and a heating mechanism that applies heat to the refiner body at a time when the adsorption ability of the water adsorbent or the $CO_2$ adsorbent drops to an amount that is less than or equal to a predetermined amount.

In accordance with this arrangement, even though an adsorption ability of the water adsorbent and the $CO_2$ adsorbent drops, since the adsorption ability can be restored by being heated, it becomes possible to measure the concentration of $CO_2$ for a long period of time without any maintenance such as exchanging the adsorbent.

In addition, there is a case that the $CO_2$ adsorbent such as zeolite also has a function of water adsorption. In this case, if the $CO_2$ adsorbent is arranged in the upstream side of the water adsorbent, the water is adsorbed by the $CO_2$ adsorbent and $CO_2$ might be failed to be sufficiently adsorbed. However, in accordance with this invention, since the water in the introduced sample gas is adsorbed in advance by the water adsorbent, the function of adsorbing $CO_2$ by the $CO_2$ adsorbent arranged in the downstream side of the water adsorbent is sufficiently exerted so that it becomes possible to refine the zero gas with high quality.

Especially, different from purification to lower a $CO_2$ concentration to be smaller than or equal to a reference value, in some cases, fluctuation of 1 ppm-10 ppm matters for the zero gas for the $CO_2$ concentration measurement device. Then the $CO_2$ concentration should not fluctuate depending on, for example, an amount of moisture in atmosphere. On this point, the effect of this invention that $CO_2$ is adsorbed by the $CO_2$ adsorbent such as zeolite after moisture is adsorbed by the water adsorbent such as silica gel, namely, the effect that the $CO_2$ concentration of the zero gas can be made substantially zero without fail irrespective of fluctuation of the moisture concentration of the sample gas becomes especially conspicuous in a field of the zero gas refiner for $CO_2$ concentration measurement device.

The above-mentioned "the zero gas containing no $CO_2$" means not only the gas whose $CO_2$ concentration is completely zero but also the gas that can be used as a reference for the $CO_2$ concentration measurement and whose $CO_2$ concentration falls within a range of substantially no influence on the measurement accuracy.

As a concrete embodiment represented is that the $CO_2$ adsorbent adsorbs $CO_2$ by making use of a molecular sieve action and a main component of the water adsorbent is silica gel, silica alumina or activated alumina. Silica gel, silica alumina or activated alumina is a substance that adsorbs a polar molecule.

In order both to eliminate useless heating and to prevent decomposition of the adsorbent due to overheating, it is preferable that the water adsorbent and the $CO_2$ adsorbent are separately housed in the refiner body, the heating mechanism is arranged in an area where the adsorbent whose restoration temperature is higher is housed and this adsorbent is heated directly by the heating mechanism, and the adsorbent whose restoration temperature is lower is heated by the remaining heat.

In order to decrease a substantial amount of adsorption treatment of the zero gas refiner and to reduce a burden for the adsorbent, it is preferable that the sample gas discharged from the $CO_2$ concentration measurement device and the zero gas are joined and introduced into the zero gas refiner.

In order to make it possible to conduct a continuous measurement, it is preferable that at least two above-mentioned zero gas refiners for $CO_2$ concentration measurement device, namely the first zero gas refiner and the second zero gas refiner are arranged in parallel, while the sample gas or the air is introduced into the first zero gas refiner and the first zero gas refiner conducts an adsorption operation of the water and $CO_2$, neither sample gas nor air is introduced into the second zero gas refiner and the second zero gas refiner conducts a restoration operation by being heated.

In this case, it is further preferable that a part of the zero gas coming from the first zero gas refiner is introduced into the second zero gas refiner as a purge gas. This is because there is no need of additionally supplying the purge gas and it is also possible to promote simplification of the device. In addition, because of the cooling effect of the purge gas it is possible to make the zero gas refiner quickly return to a state of being able to be ready for adsorption after being heated for restoration.

Effect of the Invention

In accordance with the present claimed invention having the above-mentioned arrangement, even though an adsorption ability of the water adsorbent and the $CO_2$ adsorbent drops, since the adsorption ability is restored by being heated, it becomes possible to measure the concentration of $CO_2$ for a long period of time without any maintenance such as exchanging the adsorbent.

In addition, there is a case that the $CO_2$ adsorbent such as zeolite also has a function of water adsorption. In this case, if the $CO_2$ adsorbent is arranged in the upstream side of the water adsorbent, the water is adsorbed by the $CO_2$ adsorbent and $CO_2$ might be failed to be sufficiently adsorbed by the $CO_2$ adsorbent. However, in accordance with this invention, since the water in the introduced sample gas is adsorbed in advance by the water adsorbent, the function of adsorbing $CO_2$ by the $CO_2$ adsorbent arranged in the downstream side of the water adsorbent is sufficiently exerted so that it becomes possible to refine the zero gas with high quality.

BEST MODES OF EMBODYING THE INVENTION

One embodiment of a $CO_2$ concentration measurement system in accordance with this invention will be explained with reference to drawings.

Figure 1:
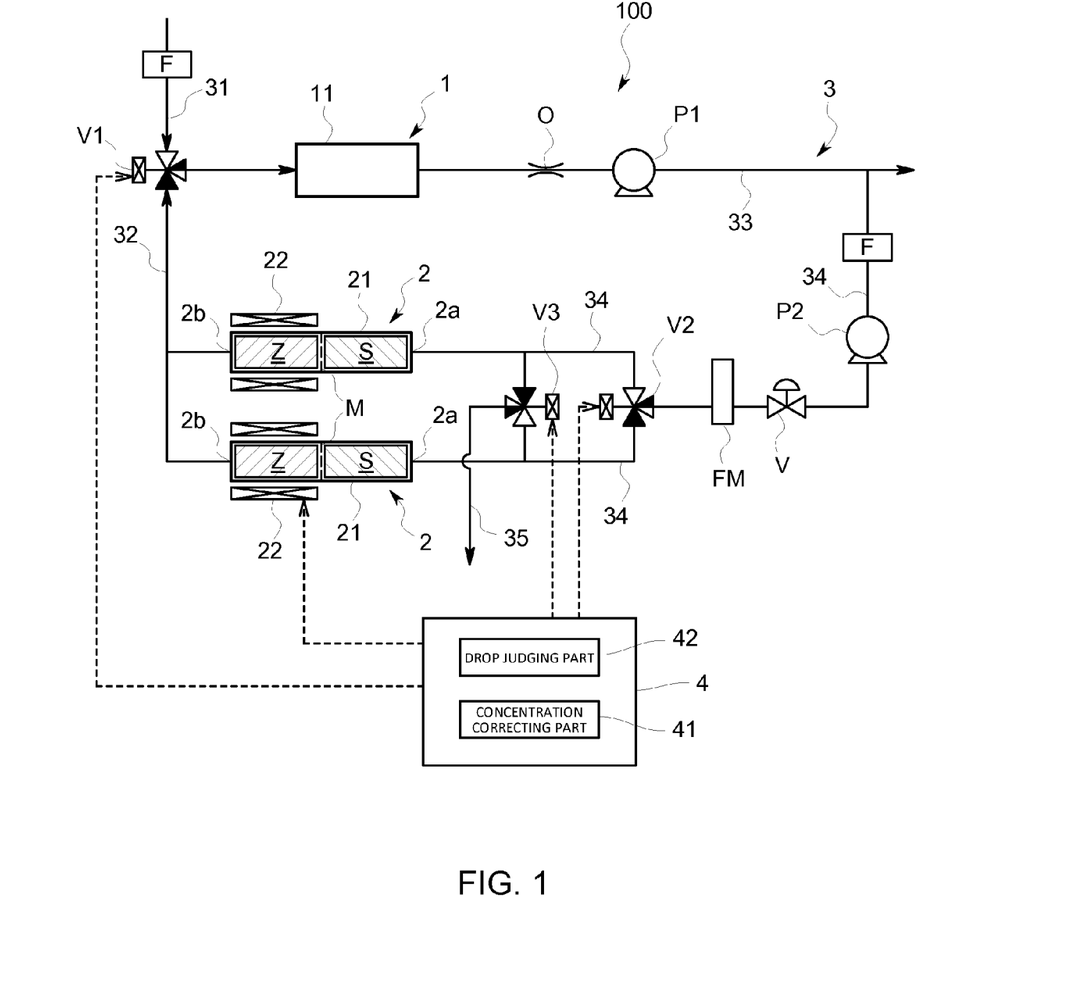
FIG. 1 is an overall pattern view showing a $CO_2$ concentration measurement system in accordance with one embodiment of this invention.

The $CO_2$ concentration measurement system 100 of this embodiment is to measure, for example, a concentration of $CO_2$ in air, and, as shown in FIG. 1, comprises a $CO_2$ concentration measurement device 1 that measures the concentration of $CO_2$ in a sample gas (air) with a reference of the $CO_2$ concentration of a zero gas that contains no $CO_2$, a zero gas refiner 2 that refines the zero gas containing no $_{CO2}$ from the sample gas and a fluid circuit 3 arranged between the $CO_2$ concentration measurement device 1 and the zero gas refiner 2. Each component will be explained in detail.

(1) $CO_2$ Concentration Measurement Device 1

The $CO_2$ concentration measurement device 1 comprises, as shown in FIG. 1, a measurement cell 11 into which the sample gas and the zero gas are introduced in turn, a $CO_2$ concentration sensor (not shown in drawings) that detects a value corresponding to a $CO_2$ concentration of the sample gas introduced into the measurement cell 11 and a value corresponding to a $CO_2$ concentration of the zero gas introduced into the measurement cell 11 respectively and a concentration correcting part 41 that corrects or calibrates the detected value of the $CO_2$ concentration detected by the $CO_2$ concentration sensor based on the detected value of the $CO_2$ concentration of the zero gas detected by the $CO_2$ concentration sensor and that calculates the $CO_2$ concentration of the sample gas.

The $CO_2$ concentration sensor is of, for example, an infrared spectroscopy method and comprises a light source (not shown in drawings) that irradiates a measurement light on inside of the cell 11, and light detector (not shown in drawings) that detects an intensity of the measurement light that passed the cell 11. The $CO_2$ concentration sensor detects the $CO_2$ concentration based on an attenuation of the measurement light detected by the light detector.

The concentration correcting part 41 produces a function of correction by an information processing circuit 4 comprising a CPU, a memory and an A/D converter or the like. More specifically, the information processing circuit 4 performs the function as the concentration correcting part 41 by cooperating with the CPU and its peripheral devices based on programs stored in the memory.

(2) Zero Gas Refiner 2

The zero gas refiner 2 comprises, as shown in FIG. 1, a water adsorbent (S) and a $CO_2$ adsorbent (Z) that desorb an adsorbed component by being heated to a predetermined restoration temperature, a refiner body 21 inside of which the water adsorbent (S) and the $CO_2$ adsorbent (Z) are included and that adsorbs water and $CO_2$ in an introduced gas by the use of the water adsorbent (S) and the $CO_2$ adsorbent (Z) and that leads out the gas as the zero gas and a heating mechanism 22 that applies heat to the refiner body 21. In this embodiment, two zero gas refiners 2, namely a first zero gas refiner 2 and a second zero gas refiner 2 are arranged in parallel.

As the water adsorbent (S) used is a silica gel whose adsorption ability can be restored by releasing the physically adsorbed water by being heated to a predetermined temperature.

As the $CO_2$ adsorbent (Z) used is a zeolite whose adsorption ability can be restored by releasing the physically adsorbed $CO_2$ by being heated to a predetermined temperature that is higher than that of the silica gel.

As the adsorbent having the physical adsorption ability represented is a molecular sieve in addition to the above-mentioned zeolite. This kind of the adsorbent has, for example, a plurality of minute bores and makes use of a molecular sieve action that selectively adsorb only a molecular whose size is small enough to enter the minute bore, and has a characteristic of being able to be easily restored by being heated unlike soda lime that adsorbs the molecular by making use of a chemical bond.

The refiner body 21 is made of, for example, a metal in a cylindrical shape, and an input port 2a into which the gas flows in is provided on one end surface and an output port 2b from which the gas flows out is provided on the other end surface. The water adsorbent (silica gel) (S) is filled into a half part, locating in the input port 2a side, of the refiner body 21 and the $CO_2$ adsorbent (zeolite) (Z) is filled into a half part, locating in the output port 2b side, of the refiner body 21. For example, a filter mesh (M) is arranged as a partition at a boundary between the water adsorbent (S) and the $CO_2$ adsorbent (Z).

The heating mechanism 22 comprises, for example, a winding heater that can be operated to be ON/OFF by an operation from the outside, and the $CO_2$ adsorbent (zeolite) (Z) is directly heated by winding the winding heater around the half part, in the output port 2b side, of the refiner body 21 and the water adsorbent (silica gel) (S) is indirectly heated by heat transfer from the refiner body 21. The heating temperature by the heating mechanism 22 is set to be higher than or equal to the minimum restorable temperature of the $CO_2$ adsorbent (zeolite) (Z) and a temperature of the water adsorbent (silica gel) (S) due to the above-mentioned heat transfer is set to be higher than or equal to the minimum restorable temperature and lower than or equal to a decomposition temperature. In this embodiment, the heating temperature by the heating mechanism 22 is, for example, 130° C.~180° C.

(3) Fluid Circuit 3

A configuration of a fluid circuit 3 that connects the above-mentioned $CO_2$ concentration measurement device 1 and the zero gas refiner 2 in view of fluid will be explained.

The fluid circuit 3 comprises a sample gas flow channel 31 into which the sample gas is introduced, a zero gas flow channel 32 where the zero gas output from the output port 2b of the zero gas refiner 2 flows, a switch valve (a three-way valve) (V1) that selectively connects either one of the sample gas flow channel 31 and the zero gas flow channel 32 to the cell 11 of the $CO_2$ concentration measurement device 1, a discharge flow channel 33 that is connected to the cell 11 of the $CO_2$ concentration measurement device 1 and a feedback flow channel 34 that branches from the discharge flow channel 33 and that is connected to an input port 2a of the zero gas refiner 2. The feedback flow channel 34 bifurcates on the way and each of the bifurcated feedback flow channels 34 is connected to the first zero gas refiner 2 and the second zero gas refiner 2 respectively and a switch valve (a three-way valve) (V2) is arranged at this junction so that the discharge flow channel 33 is selectively connected to either one of the first zero gas refiner 2 and the second zero gas refiner 2. In addition, the bifurcated feedback flow channel 34 that is not connected to the discharge flow channel 33 is connected to a purge gas discharge flow channel 35 by a switch valve (V3).

A movement of the switch valve (V1)~(V3) and an ON/OFF movement of the heating mechanism 22 are automatically controlled by the information processing circuit 4 (or a control device that is additionally provided). In addition, a code (F) denotes a filter, codes (P1) and (P2) denote a pump, a code (O) denotes an orifice, a code (V) denotes a flow rate control valve and a code (FM) denotes a flow measurement device.

(4) Movement

Next, a movement of the above-mentioned $CO_2$ concentration measurement system 100 will be explained with reference to state transition views and timing charts shown in FIG. 2 FIG. 8.

Figure 2:
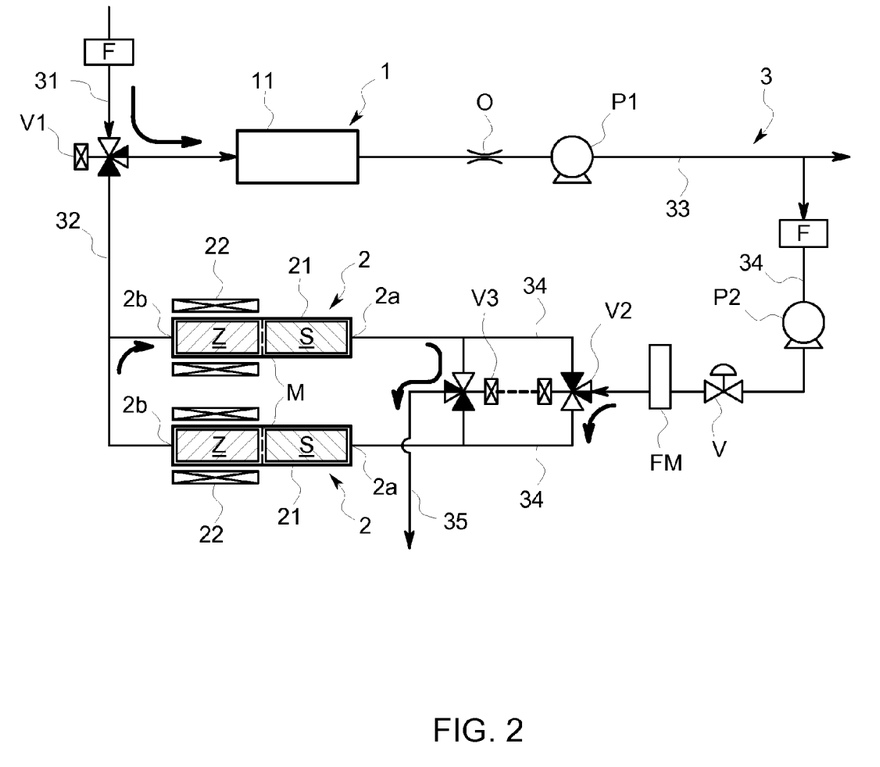
FIG. 2 is an overall pattern view to explain a movement of the $CO_2$ concentration measurement system in accordance with this embodiment.

First, in the first cycle, the sample gas flow channel 31 and the $CO_2$ concentration measurement device 1 are connected as shown in FIG. 2 so that the sample gas is introduced into the cell 11 of the $CO_2$ concentration measurement device 1. At this time, the $CO_2$ concentration of the sample gas is detected by the $CO_2$ concentration sensor of the $CO_2$ concentration measurement device 1 and the detected $CO_2$ concentration is stored in the memory of the information processing circuit 4. A flow rate of the sample gas introduced into the $CO_2$ concentration measurement device 1 is set at a predetermined value (for example, 2 multiplied by Q) by the orifice (O) and the pump (P1) arranged on the discharge flow channel 33.

The sample gas passing the $CO_2$ concentration measurement device 1 is discharged from the discharge flow channel 33, and a part of the sample gas is introduced into the first zero gas refiner 2 after passing the feedback flow channel 34. The flow rate of the sample gas introduced into the first zero gas refiner 22 is set at a predetermined value by the pump (P2) and an opening degree of the flow rate valve (V) arranged on the feedback flow channel 34.

A moving state of the heating device of the first zero gas refiner 2 into which the sample gas is introduced is set to be OFF and the first zero gas refiner 2 makes the introduced sample gas as the zero gas and outputs the zero gas. All of the zero gas flows into the refiner body 21 through the output port 2b of the second zero gas refiner 2 and purges inside of the refiner body 21 of the second zero gas refiner 2 and then is discharged from the purge gas discharge flow channel 35 through the input port 2a of the second zero gas refiner 2.

Figure 3:
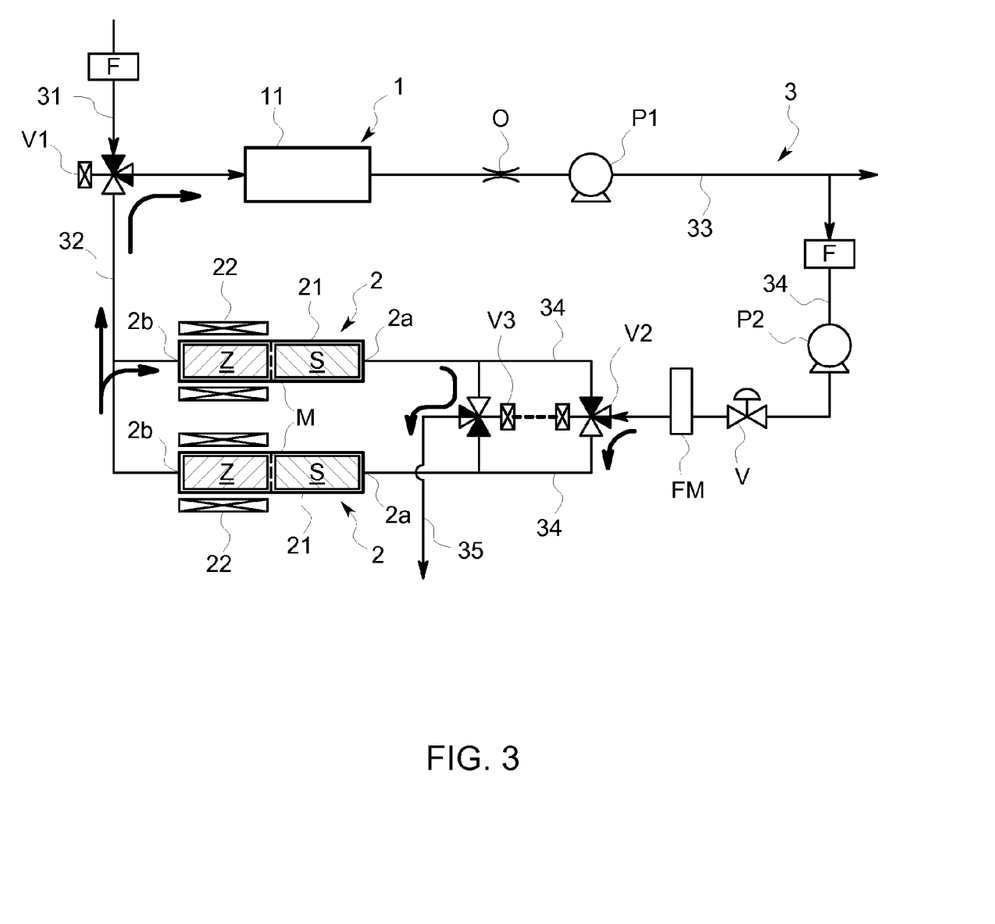
FIG. 3 is an overall pattern view to explain the movement of the $CO_2$ concentration measurement system in accordance with this embodiment.

Next, after passing a predetermined time period (t) (for example, several seconds several minutes) the switch valve (V1) is switched so that the zero gas flow channel 32 is connected to the $CO_2$ concentration measurement device 1 as shown in FIG. 3. As a result of this, a part of the zero gas output from the first zero gas refiner 2 flows into the $CO_2$ concentration measurement device 1 and remaining zero gas flows into the second zero gas refiner 2 as a purge gas. A flow rate of the zero gas flowing into the $CO_2$ concentration measurement device 1 is a predetermined value determined by the orifice (O) and the pump (P1) arranged on the discharge flow channel 33 and is a flow rate (2 multiplied by Q) equal to the flow rate of the sample gas.

At this time, the $CO_2$ concentration of the zero gas is detected by the $CO_2$ concentration sensor of the $CO_2$ concentration measurement device 1 and the detected value is stored in the memory of the information processing unit 4. Then, a concentration correction part 41 of the information processing circuit 4 corrects the detected value of the $CO_2$ concentration of the sample gas stored in the memory in the previous cycle by the use of the detected value of the $CO_2$ concentration of the zero gas detected in this cycle, and stores the corrected value as the measurement value of the $CO_2$ concentration of the sample gas together with other measurement condition such as the time of measurement or the like.

The zero gas passing the $CO_2$ concentration measurement device 1 is discharged from the discharge flow channel 33 and a part of the zero gas passes the feedback flow channel 34 and is introduced into the first zero gas refiner 2. A flow rate of the zero gas introduced into the first zero gas refiner 2 is the same as the flow rate of the sample gas. Although the first zero gas refiner 2 into which the zero gas is introduced is in the moving state, since the zero gas flows into the first zero gas refiner 2, the water adsorbent and the $CO_2$ adsorbent in the inside of the first zero gas refiner 2 do not substantially function and are output to the zero gas flow channel 32 as they are.

Next, after passing the predetermined time period (t), the switch vale (V1) is switched again and the sample gas flow channel 31 is connected to the $CO_2$ concentration measurement device 1 as shown in FIG. 2, and the same cycle as that of the above is operated. Then, with this operation, the measurement value of the $CO_2$ concentration of the sample gas is stored one after another at a constant cycle. The continuous measurement value of the $CO_2$ concentration is output to, for example, a display or a printer as a numerical value respectively, or as a continuous time series transition graph.

Figure 4:
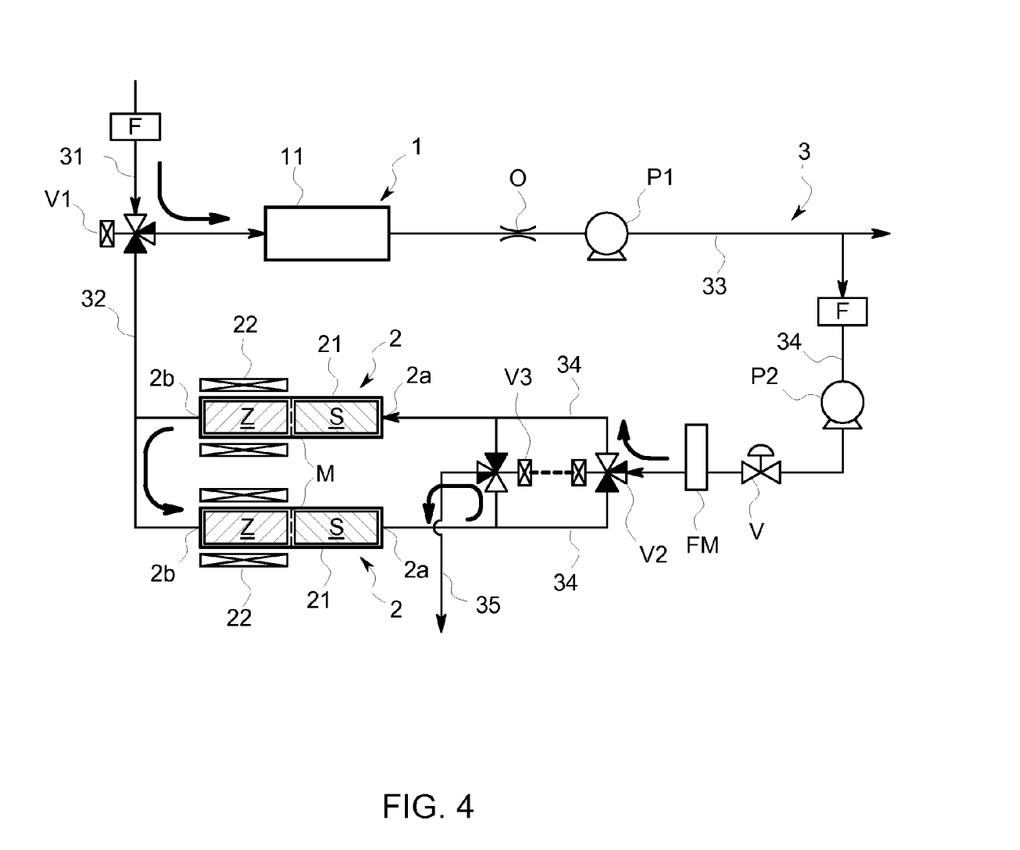
FIG. 4 is an overall pattern view to explain the movement of the $CO_2$ concentration measurement system in accordance with this embodiment.

If the above-mentioned cycles are repeated, since the adsorption ability of the $CO_2$ adsorbent (Z) and the water adsorbent (S) of the first zero gas refiner 2 drops, the drop judging part 42 of the information processing circuit 4 judges that the adsorption ability of the $CO_2$ adsorbent (Z) and the water adsorbent (S) drops. Concretely, in case that the drop judging part 42 judges that the adsorption ability of the $CO_2$ adsorbent (Z) and the water adsorbent (S) drops to an amount that is less than or equal to a predetermined amount, the information processing unit 4 switches the switch valves (V2) and (V3) so as to connect the discharge flow channel 33 to the second zero gas refiner 2 and to set the heating device of the first zero gas refiner 2 to be ON. For example, in case that the drop judging part 42 judges that a certain period of time passes, or a certain cycle passes, the drop judging part 42 judges that the adsorption ability drops to an amount that is less than or equal to the predetermined amount. With this judgment, the refiner body 21 of the first zero gas refiner 2 is heated so that the restoration of the $CO_2$ adsorbent (Z) and the water adsorbent (S) is initiated. $CO_2$ and the water vapor discharged from the $CO_2$ adsorbent (Z) and the water adsorbent (S) at this time are discharged from the purge gas discharge flow channel 35 together with the zero gas (purge gas) output from the second zero gas refiner 2. A period of heating is until completion of the restoration, and the flow rate, an amount of the $CO_2$ adsorbent (Z) and an amount of the water adsorbent (S) are so set to make the period of heating shorter than the above-mentioned certain period of time. Also during this time period, a cross flow cycle is conducted by switching the switch valve (V1) at every predetermined time period (t) and a measurement value of the $CO_2$ concentration of the sample gas is stored one after another in a constant period.

Figure 5:
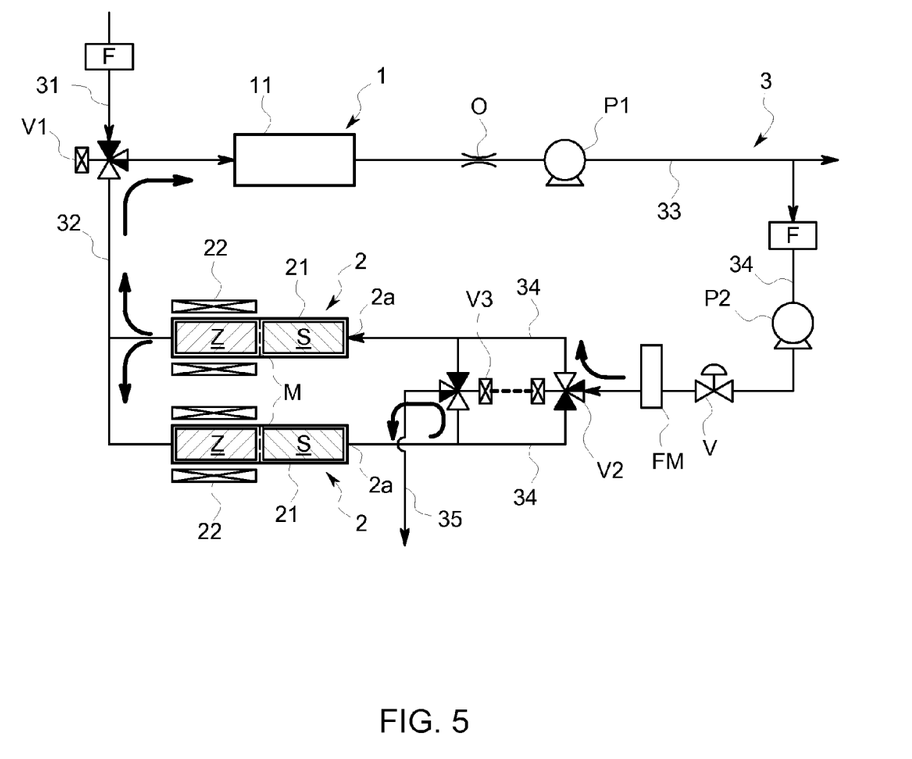
FIG. 5 is an overall pattern view to explain the movement of the $CO_2$ concentration measurement system in accordance with this embodiment.
Figure 6:
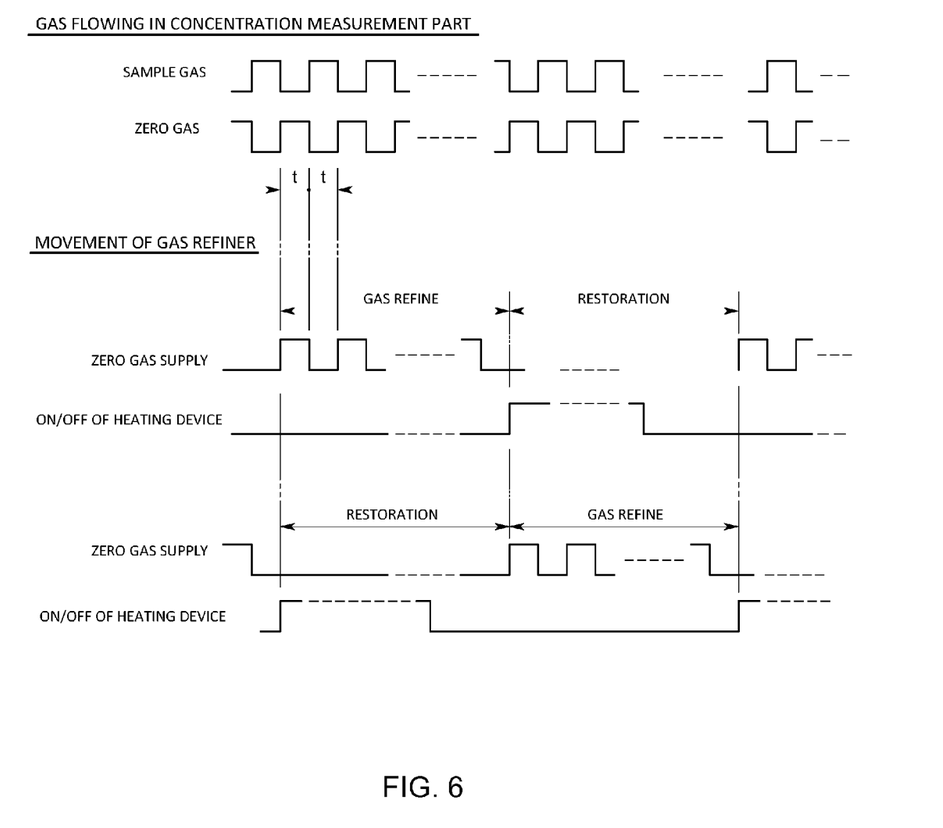
FIG. 6 is a timing chart to explain the movement of the $CO_2$ concentration measurement system in accordance with this embodiment.

Later, after passing a predetermined time period (or after passing a predetermined cycle), in case that the drop judging part 42 judges that the adsorption ability of the $CO_2$ adsorbent (Z) and the water adsorbent (S) drops to an amount that is less than or equal to the predetermined amount, the information processing circuit 4 switches the switch valves (V2) and (V3) so that the discharge flow channel 33 is connected to the first zero gas refiner 4 whose adsorption ability is restored and the heating device of the second zero gas refiner 2 is set to be ON. This process is repeated.

(5) Effect

In accordance with the $CO_2$ concentration measurement system 100 having the above-mentioned arrangement, following effects are stored.

Even though an adsorption ability of the water adsorbent and the $CO_2$ adsorbent drops, since the adsorption ability is restored by being heated, it becomes possible to measure the concentration of $CO_2$ for a long period of time without any maintenance such as exchanging the adsorbent.

In addition, there is a case that the $CO_2$ adsorbent (Z) such as zeolite also has a function of water adsorption. In this case, if the $CO_2$ adsorbent (Z) is arranged in the upstream side of the water adsorbent, the water is adsorbed by the $CO_2$ adsorbent (Z) and $CO_2$ might be failed to be sufficiently adsorbed. However, in accordance with the $CO_2$ concentration measurement system 100 of this invention, since the water in the introduced sample gas is adsorbed in advance by the water adsorbent (S), the function of adsorbing $CO_2$ by the $CO_2$ adsorbent (Z) arranged in the downstream side of the water adsorbent (S) is sufficiently exerted so that it becomes possible to refine the zero gas with high quality.

Since the water adsorbent (S) and the $CO_2$ adsorbent (Z) are housed separately in the refiner body 21 and the heating mechanism 22 is arranged in an area where the $CO_2$ adsorbent (Z) whose restoration temperature is high is housed and the $CO_2$ adsorbent (Z) is directly heated by the heating mechanism 22 and the water adsorbent (S) whose restoration temperature is low is heated by the remaining heat, unnecessary heating can be avoided so that it is possible to prevent decomposition of the water adsorbent (S) due to overheating.

Since the feedback flow channel 34 is arranged and the sample gas and the zero gas discharged from the $CO_2$ concentration measurement device 1 join and are introduced into the zero gas refiner 2, a substantial amount of the adsorption treatment in the zero gas refiner 2 decreases so that it is possible to reduce a burden for the adsorbent.

Figure 7:
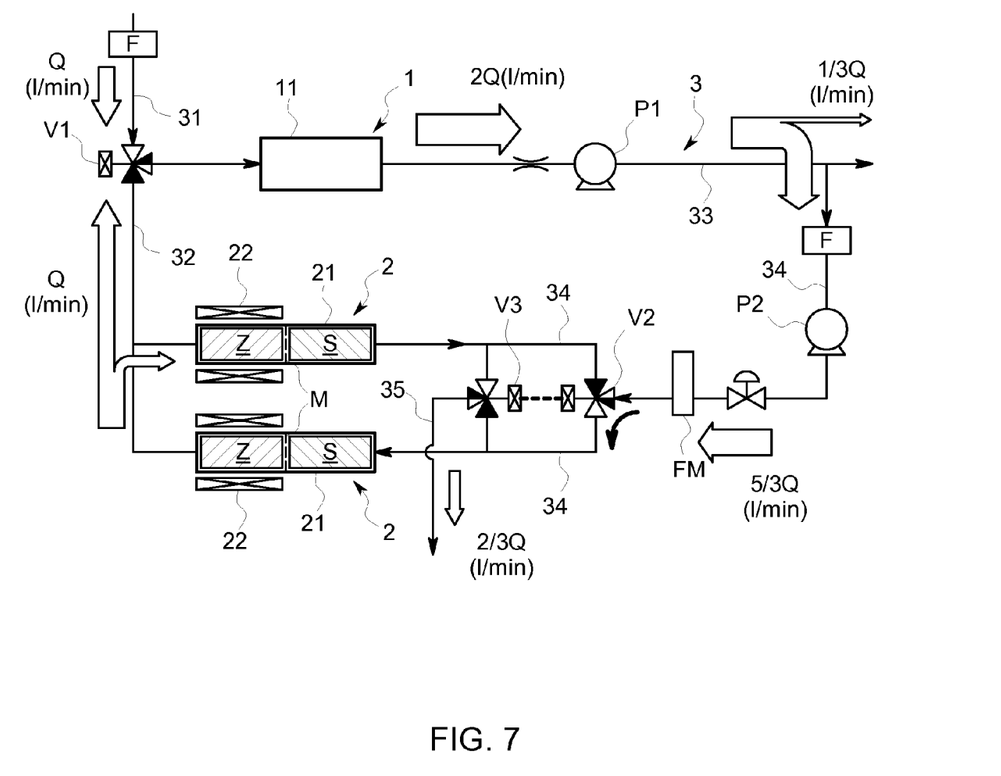
FIG. 7 is an overall pattern view to explain a flow rate flowing in each flow channel of the $CO_2$ concentration measurement system in accordance with this embodiment.

This reason will be explained with reference to FIG. 7. The flow rate flowing in the cell 11 and the discharge flow channel 33 is 2 by Q. When the gas flows, each of the flow rate flowing in the sample gas flow channel 31 and the flow rate flowing in the zero gas flow channel 32 is 2 by Q. However, there is a time period when no gas flows due to the switch valve (V1) so that the average flow rate in the sample gas flow channel 31 and the average flow rate in the zero gas flow channel 32 become Q respectively.

A mixed gas composed of the sample gas and the zero gas with a ratio of 1 to 1 (strictly speaking, different depending on time) flows in the discharge flow channel 33 and when a part of (for example, 5/3Q in FIG. 7) the mixed gas flows in the feedback flow channel 34, the mixed gas is introduced into the zero gas refiner 2. Practically the $CO_2$ concentration in the sample gas refined by the zero gas refiner 2 is only a half of the newly introduced sample gas. As mentioned, the practical amount of the adsorption treatment in the zero gas refiner 2 decreases so that it is possible to reduce a burden for the adsorbent.

Since the first zero gas refiner 2 and the second zero gas refiner 2 are arranged in parallel and while the first zero gas refiner 2 conducts a zero gas refining movement (an adsorption movement), the second zero gas refiner 2 conducts a reproducing movement and these movements are repeated in turn, it becomes possible to conduct the measurement continuously without any breaks of zero gas refining.

Since a part of the zero gas coming from the first zero gas refiner 2 is introduced into the second zero gas refiner 2 as the purge gas, there is no need of additionally supplying the purge gas and it is also possible to promote simplification of the device. In addition, because of the cooling effect of the purge gas it is possible to make the zero gas refiner 2 quickly return to a state of being able to be ready for adsorption after being heated for restoration.

(6) Modified Embodiment

The present claimed invention is not limited to the above-mentioned embodiment. For example, a pipe for introducing the sample gas or the atmosphere may be provided instead of the feedback flow channel 34 and the zero gas may be refined from the introduced sample gas or the introduced atmosphere and may be discharged directly. In this case, the adsorption ability of the $CO_2$ adsorbent (Z) and the water adsorbent (S) drop more quickly because much more (two times) sample gas than that of the above-mentioned embodiment is required to be treated by the zero gas refiner 2.

Figure 8:
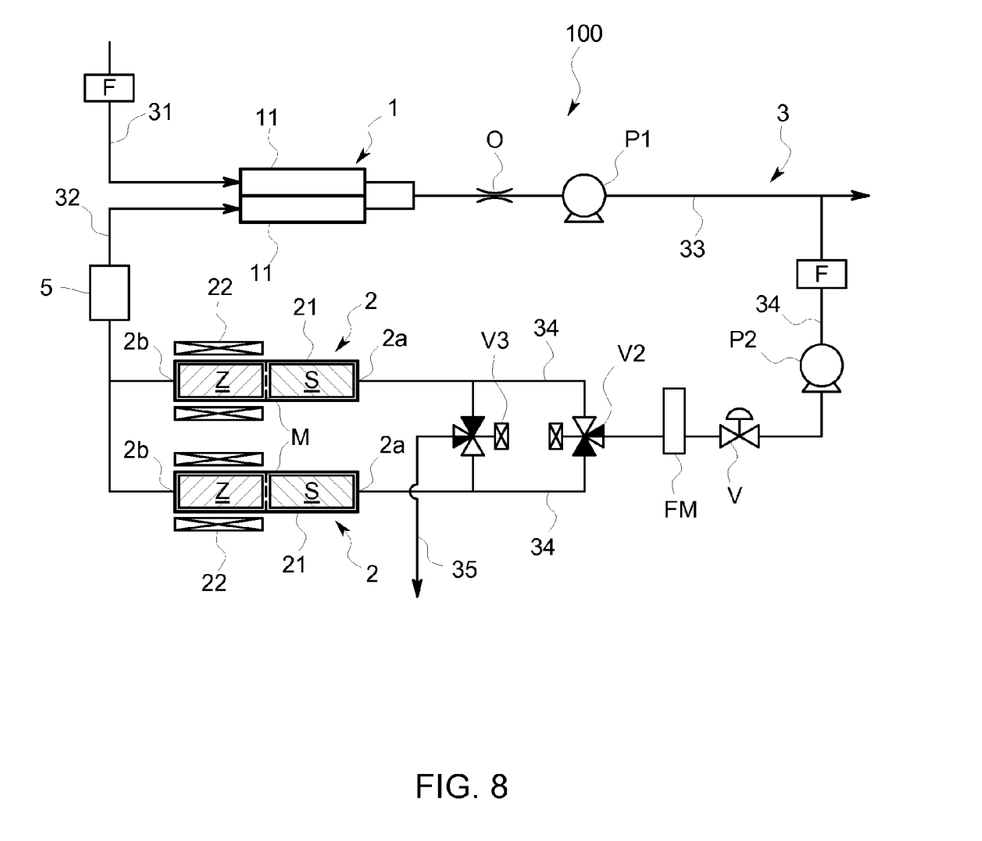
FIG. 8 is an overall pattern view showing a $CO_2$ concentration measurement system in accordance with other embodiment of this invention.

In addition, as shown in FIG. 8, two cells 11, in other words, a first cell 11 and a second cell 11 may be arranged in parallel in the $CO_2$ concentration measurement device 1 and the sample gas may be introduced into the first cell 11 and the zero gas may be introduced into the second cell 11. In accordance with this arrangement, it is possible to flow the gas continuously without switching the zero gas and the sample gas.

Furthermore, as shown in FIG. 8, a $CO_2$ monitor 5 may be provided in the downstream of the $CO_2$ adsorbent (Z) and the water adsorbent (S). In accordance with this arrangement, it is possible for the $CO_2$ monitor 5 to detect that the adsorbent ability of the $CO_2$ adsorbent (Z) and the water adsorbent (S) drops to an amount that is equal to or less than the predetermined amount without providing the information processing unit 4 with the drop judging part 42. If the $CO_2$ monitor 5 is provided in the flow channel configuration shown in FIG. 1, it is also possible to detect that the adsorbent ability of the $CO_2$ adsorbent (Z) and the water adsorbent (S) drops to an amount that is equal to or less than the predetermined amount. The $CO_2$ monitor 5 may be, for example, a coloring $CO_2$ adsorbent or a $CO_2$ analyzer. The $CO_2$ monitor 5 may be arranged on the zero gas flow channel 32 or on a by-pass flow channel that joins after bifurcated from the zero gas flow channel 32.

The zero gas refiner may be a single, or three or more zero gas refiners may be arranged in parallel.

In addition, the present claimed invention is not limited to the above-mentioned embodiment and may be variously modified without departing from a spirit of the invention.

EXPLANATION OF CODES

100 . . . $CO_2$ concentration measurement system
1 . . . $CO_2$ concentration measurement device
2 . . . zero gas refiner
S . . . water adsorbent
Z . . . $CO_2$ adsorbent
21 . . . refiner body
22 . . . heating mechanism
42 . . . drop judging part

What is claimed is:

1. A $CO_2$ concentration measurement system comprising:
a $CO_2$ concentration measurement device that has a measurement cell into which a sample gas containing $CO_2$ or a zero gas containing no $CO_2$ is introduced, and that measures a concentration of the $CO_2$; and
one or multiple zero gas refiners for the $CO_2$ concentration measurement device that refines the zero gas as being a reference of a measurement and supplies the measurement cell,
wherein each of the one or multiple zero gas refiners includes
a refiner body,
a water adsorbent and a $CO_2$ adsorbent, housed inside of the refiner body, that desorb an adsorbed component and restore an adsorption ability by being heated to a predetermined restoration temperature, and
a heating mechanism that applies heat to the refiner body at a time when the adsorption ability of the water adsorbent or the $CO_2$ adsorbent drops to an amount that is less than or equal to a predetermined amount,
wherein the refiner body is configured to introduce air into the water absorbent first and into the $CO_2$ adsorbent second, and
wherein the one or multiple zero gas refiners is connected to a zero gas flow channel that directs the zero gas refined by the one or multiple zero gas refiners to the measurement cell.

2. The $CO_2$ concentration measurement system described in claim 1, wherein
the $CO_2$ adsorbent adsorbs $CO_2$ by making use of a molecular sieve action.

3. The $CO_2$ concentration measurement system described in claim 1, wherein
a main component of the water adsorbent is silica gel, silica alumina, or activated alumina.

4. The $CO_2$ concentration measurement system described in claim 1 further comprising a drop judging part that makes a judgment that the adsorption ability of the water adsorbent or the $CO_2$ adsorbent drops to the amount that is less than or equal to the predetermined amount.

5. The $CO_2$ concentration measurement system described in claim 1, wherein
the water adsorbent and the $CO_2$ adsorbent are separately housed in the refiner body, the heating mechanism is arranged in an area where the adsorbent whose restoration temperature is higher is housed and this adsorbent is heated directly by the heating mechanism, and the adsorbent whose restoration temperature is lower is heated by remaining heat.

6. The $CO_2$ concentration measurement system described in claim 1, wherein
the sample gas and the zero gas discharged from the $CO_2$ concentration measurement device are introduced into the one or multiple zero gas refiners.

7. The $CO_2$ concentration measurement system described in claim 1, wherein the one or multiple zero gas refiners are arranged in parallel, while the sample gas or the air is introduced into a first of the one or multiple zero gas refiners conducting an adsorption operation of water and $CO_2$, and neither the sample gas nor the air is introduced into a second of the zero gas refiners conducting a restoration operation by being heated.

8. The $CO_2$ concentration measurement system described in claim 7, wherein
   a part of the zero gas discharged from the first of the one or multiple zero gas refiners is introduced into the second of the one or multiple zero gas refiners as a purge gas.

* * * * *